United States Patent [19]

Spivack et al.

[11] Patent Number: 4,552,926
[45] Date of Patent: Nov. 12, 1985

[54] SUBSTITUTED 4-HYDROXYPHENYLTHIO BENZOATE STABILIZERS

[75] Inventors: John D. Spivack; Stephen D. Pastor, both of Spring Valley, N.Y.

[73] Assignee: Ciba-Geigy Corporation, Ardsley, N.Y.

[21] Appl. No.: 536,069

[22] Filed: Sep. 26, 1983

[51] Int. Cl.$^4$ .............................. C08K 5/20; C08K 5/36
[52] U.S. Cl. ................................ 524/219; 260/455 R; 524/222; 524/283; 524/289; 560/66; 560/72; 564/177; 564/179
[58] Field of Search .................... 260/455 R; 524/219, 524/221, 248, 283, 289, 330, 331, 291; 560/66, 72; 564/177, 179

[56] References Cited

U.S. PATENT DOCUMENTS

| | | | |
|---|---|---|---|
| 3,285,855 | 11/1966 | Dexter et al. | 524/291 |
| 3,944,594 | 3/1976 | Kleiner et al. | 524/283 |
| 4,108,831 | 8/1978 | Cottman | 524/330 |
| 4,120,846 | 10/1978 | Spivack et al. | 524/289 |
| 4,128,530 | 12/1978 | Cottman | 524/330 |
| 4,311,637 | 1/1982 | Cottman | 524/330 |

FOREIGN PATENT DOCUMENTS 42-6332 3/1967 Japan.

OTHER PUBLICATIONS

CA 67, 73382u, (1967).

Primary Examiner—Veronica P. Hoke
Attorney, Agent, or Firm—Luther A. R. Hall; Harry Falber

[57] ABSTRACT

The title compounds correspond to the formula

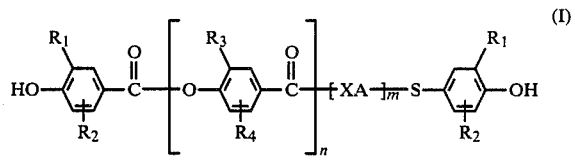

wherein $R_1$, $R_2$, $R_3$ and $R_4$ are alkyl, A is alkylene, X is —NH— or —S—, m is 1 and n is 0 or 1, and are useful as stabilizers for organic polymers and lubricating oils to counteract the degradative effects of heat, light and air.

9 Claims, No Drawings

SUBSTITUTED 4-HYDROXYPHENYLTHIO BENZOATE STABILIZERS

Organic polymeric materials such as plastics and resins, and lubricating and mineral oils are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined that the 4-hydroxyphenylthio benzoates of this invention possess an unusual combination of desirable properties which make them particularly effective and useful as stabilizers. The compounds are particularly effective in protecting polyolefins, high impact polystyrene, rubbers such as polybutadiene and styrene-butadiene rubber, and other elastomers wherein retention of elasticity and inhibition of cross-linking, crazing, discoloration, odor formation and exudation are basic requirements.

A number of mercaptophenol derivatives have been previously disclosed. Many of these derivatives are, however, hydroxyphenylthio alkanoate esters. Polyphenolic hydroxyphenylthio alkanoate esters are disclosed in U.S. Pat. No. 4,311,637.

It is the primary object of this invention to provide a class of hydroxyphenylthio benzoate esters which exhibit a broad range of improved stabilization performance characteristics.

Various other objects and advantages of this invention will become evident from the following description thereof.

The compounds of this invention correspond to the formula I

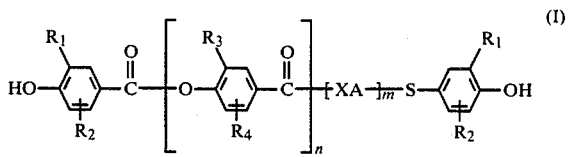

wherein
R, $R_2$, $R_3$ and $R_4$ are independently hydrogen, alkyl of 1 to 12 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms;
X is —NH—, —O— or —S—;
A is alkylene of 1 to 10 carbon atoms, phenylene or cycloalkylene of 5 to 6 carbon atoms and
n and m independently are 0 or 1.

Preferred compounds within the above structure are those wherein $R_3$ and $R_4$ are the same as $R_1$ and $R_2$ respectively and all of them are in the ortho position to the hydroxy group.

As $C_1$–$C_{12}$ alkyl the $R_1$, $R_2$, $R_3$ and $R_4$ groups are straight-chain or branched alkyl, preferably with 1 to 8 carbon atoms, such as methyl, n-butyl, sec-butyl, tert-butyl, tert-pentyl, hexyl, 2-ethylhexyl, n-octyl and 1,1,3,3-tetramethylbutyl. Tert-butyl is particularly preferred.

When $R_1$, $R_2$, $R_3$ and $R_4$ are aralkyl they represent benzyl, α-methylbenzyl or α,α-dimethylbenzyl. Substituted phenyl can be for example tolyl, mesityl or xylyl.

As $C_1$–$C_{10}$ alkylene A can be straight-chain or branched alkylene, preferably with 2 to 6 carbon atoms and is for example ethylene, propylene, trimethylene, tetramethylene, 2,2-dimethylpropane-1,3-diyl, pentamethylene or hexamethylene, ethylene being especially preferred. A as cycloalkylene is e.g. cyclopentylene or preferably cyclohexylene.

X is preferably oxygen.

Preferred compounds are those of formula I wherein n is 1.

The compounds of this invention when $R^1$ and $R^2$ are different from $R^3$ and $R^4$ can be prepared by reacting a hindered phenolic acid halide such as e.g. 3,5-di-tert-butyl-4-hydroxybenzoylchloride with an appropriate alkyl substituted hydroxy benzoate at a temperature of from about 50° to 200° C. followed by hydrolysis to the acid.

Compounds where $R^1$ and $R^2$ are the same as $R^3$ and $R^4$ can be prepared by reacting two moles of a dialkyl substituted hydroxybenzoyl halide with one mole of a base to yield an intermediate compound which is (dialkyl substituted hydroxybenzoyloxy)dialkyl benzoyl halide. The basic materials which can be employed are trialkyl amines such as triethyl amine, tripropyl amine, triisopropyl amine, tributyl amine, triamyl amine, sodium or potassium hydroxide, sodium or potassium carbonates or other similar proton acceptors.

Both syntheses of the intermediate benzoyloxybenzoic acid mentioned above can be carried out in a non-reactive solvent such as a hydrocarbon as for example, hexane, cyclohexane, heptane, non-reactive chlorinated hydrocarbon, mineral oil, and preferably benzene or toluene.

The intermediate benzoyloxybenzoic acid II (or acid halide III)

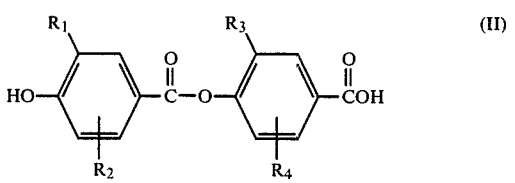

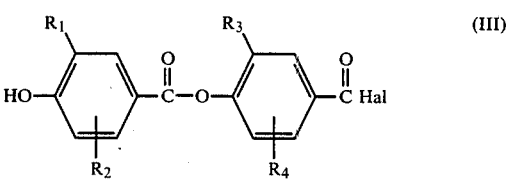

or benzoic acid IV (or acid halide V)

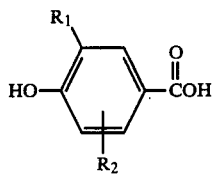

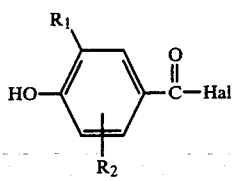

is then reacted with dialkyl-4-mercaptophenols (VI)

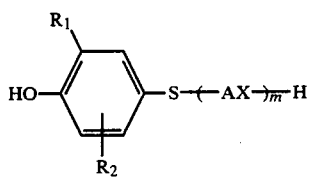

by known methods (see e.g. J. March, Advanced Organic Chemistry, McGraw-Hill, NY, 1977) to prepare the compounds of this invention.

The starting materials utilized to prepare these compounds are items of commerce or can be prepared by known methods.

Compounds of this invention are particularly effective in stabilizing organic materials such as plastics, polymers and resins in addition to mineral and synthetic fluids such as lubricating oils, circulating oils, etc.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under (1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl, acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or α-methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene. p0 6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.
8. Polymers which are derived from α,β-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as a comonomer.
13. Polyphenylene oxides and sulfides, and mixtures of polyphenylene oxides with polystyrene.
14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4,-trimethylhexamethylene terephthalamid or poly-m-phenylene isophthalamide, as well as copolymers thereof with polyethers, such as for instance, with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2,-(4-hydroxyphenyl)-propane] terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.
23. Thermosetting acrylic resins, derived from substituted acrylic esters, such as epoxy-acrylates, urethane-acrylates or polyesteracrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.
29. Aqueous emulsions of natural or synthetic rubber, e.g. natural latex or latices of carboxylated styrene-/butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants
1.1 Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol
  1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol
  1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)
  1.4. Alkyliden-bisphenols, for example,
2,2'-methylene-bis-(6-tert.butyl-4-methylphenol)
2,2'-methylene-bis-(6-tert.butyl-4-ethylphenyl)
2,2'-methylene-bis-[4-methyl-6-(Δ-methylcyclohexyl)-phenyl]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl)-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrat]
di-(3-tert.butyl-4-hydroxy-5-methylphenyl)-dicyclopentadien
di-[2-(3'-tert.butyl-2'-hydroxy-5'-methyl-benzyl)-6-tert.butyl-4-methylphenyl]-terephthalate.
  1.5. Benzylcompounds, for example,
1,3,5-tri-(3,5-di-tert.butyl-4-hydroxybenzyl)-2,4,6-trimethylbenzene-di-(3,5-di-tert.butyl-4-hydroxybenzyl)-sulfide
3,5-di-tert.butyl-4-hydroxybenzyl-mercapto-acetic acid-isooctyl ester
bis-(4-tert.butyl-3-hydroxy-2,6-dimethylbenzyl)dithiolterephthalate
1,3,5-tris-(3,5-di-tert.butyl-4-hydroxybenzyl)-isocyanurate 1,3,5-tris-(4-tert.butyl-3-hydroxy-2,6-dimethylbenzyl)-isocyanurate 3,5-di-tert.butyl-4-hydroxybenzyl-phosphoric acid-dioctadecyl ester 3,5-di-tert.butyl-4-hydroxybenzyl-phosphoric acid-monoethyl ester, calcium-salt 1.6. Acylaminophenols, for example, 4-hydroxy-lauric acid anilide 4-hydroxy-stearic acid anilide 2,4-bis-octylmercapto-6-(3,5-tert.butyl-4-hydroxyanilino)-s-triazine octyl-N-(3,5-di-tert.butyl-4-hydroxyphenyl)-carbaminate 1.7. Esters of β-(3,5-di-tert.butyl-4-hydroxyphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, di-hydroxyethyl oxalic acid, diamide.

1.8. Ester of β-(5-tert.butyl-4-hydroxy-3-methylphenyl)propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanorate, thiodiethyleneglycol, di-hydroxyethyl oxalic acid, diamide.

1.9. Amides of β-(3,5-di-tert.butyl-4-hydroxyphenyl)-propionic acid for example, N,N'-di-(3,5-di-tert.butyl-4-hydroxyphenylpropionyl)-hexamethylenediamine N,N'-di-(3,5-di-tert.butyl-4-hydroxyphenylpropionyl)-trimethylenediamine N,N'-di-(3,5-di-tert.butyl-4-hydroxyphenylpropionyl)-hydrazine 2. UV absorbers and light stabilisers 2.1. 2-(2'-Hydroxyphenyl)-benztriazoles for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy-, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxyderivative.

2.3. Esters of optionally substituted benzoic acids for example, phenyl salicylate, 4-tert.butyl-phenylsalicilate, octylphenyl salicylate, dibenzoylresorcinol, bis-(4-tert.butylbenzoyl)-resorcinol, benzoylresorcinol, 2,5-di-tert.-butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

2.6. Sterically hindered amines, for example
bis-(2,2,6,6-tetramethylpiperidyl)-sebacate
bis-(1,2,2,6,6-pentamethylpiperidyl)-sebacate
n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone).

2.7. Oxalic acid diamides, for example, 4,4'-dioctyloxy-oxanilide, 2,2'-di-octyloxy-5,5'-di-tert.butyloxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho-and para-methoxy- as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythrit diphosphite, tris-(2,4-di-tert.butylphenyl) phosphite, di-isodecylpentaerythrit diphosphite, di-(2,4-di-tert.butylphenyl)pentaerythrit diphosphite, tristearylsorbite triphosphite, tetrakis-(2,4-di-tert.butylphenyl)-4,4'-biphenylylen diphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythrit-tetrakis-(β-dodecylmercapto)-propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

6. Fillers and reinforcing agents, for example, calcium carbonate, silicates, glass fibres, asbestos, talc, kaolin, mica, barium sulfate, metal oxides and hydroxydes, carbon black, graphite.

10 Other additives, for example, plasticizers, lubricants, emulsifiers, pigments, optical brighteners, flameproofing agents, anti-static agents blowing agents and thiosynergists such as dilaurylthiodipropionate or distearylthiodipropionate.

9

The following examples illustrate the embodiments of this invention. In these examples, all parts given are by weight unless otherwise specified.

EXAMPLE 1

2-(3,5-Di-tert-butyl-4-hydroxyphenylthio)ethyl 3,5-Di-tert-butyl-4-(3,5-di-tert-butyl-4-hydroxybenzoyloxy)benzoate A solution of 13.4 g of 3,5-di-tert-butyl-4-hydroxybenzoyl chloride in 100 ml of dry toluene was added at 10°–15° C. to a solution of 3.03 g of triethylamine in 20 ml of toluene within a ten minute period. The reaction mixture was stirred at room temperature for three hours. To the reaction mixture was added 3.03 g of triethylamine and then it was treated dropwise at 20°–25° C. over seven minutes with a solution of 7.1 g of 2(3,5-tert-butyl-4-hydroxyphenyl-thio)-ethanol in 30 ml of toluene. The reaction was heated to 60°–65° C. for 90 minutes and then stirred at room temperature for 15 hours. The suspension of triethylamine hydrochloride was removed by filtration and the solvent was removed in vacuo. The residue was recrystallized from a acetonitrile to give 9.0 g (48%) of white crystals, mp 168°–170° C.

Anal. Calcd. for $C_{46}H_{66}O_6S$: C, 74.0; H, 8.9. Found: C, 74.1; H, 8.7.

EXAMPLE 2

S-(3,5-Di-tert-butyl-4-hydroxyphenyl) 3,5-Di-tert-butyl-4-(3,5-di-tert-butyl-4-hydroxybenzoyloxy)thiobenzoate The procedure of Example 1 was followed using 16.1 g of 3,5-di-tert-butyl-4-hydroxybenzoyl chloride, 7.3 g of 2,6-di-tert-butyl-4-mercaptophenol and 7.1 g of triethylamine. The residue was recrystallized from a 2-propanol:toluene mixture to give 15.6 (74%) of a white solid, mp 228°–230° C.

Anal. Calcd. for $C_{44}H_{62}O_5S$: C, 75.2; H, 8.9. Found: C, 75.1; H, 8.9.

EXAMPLE 3

2-(3,5-Di-tert-butyl-4-hydroxyphenylthio)ethyl 3,5-Di-tert-butyl-4-hydroxybenzoate A solution of 9.8 g of 2-(3,5-di-tert-butyl-4-hydroxyphenylthio) ethanol and 3.1 g of pyridine in 40 ml of toluene was added at 15°–20° C. over five minutes to a solution of 9.4 g of 3,5-di-tert-butyl-4-hydroxybenzoyl chloride in 50 ml of toluene. The reaction mixture was stirred at room temperature for 15 hours and then the resultant precipitate of triethylamine hydrochloride was removed by filtration. The solvent was removed in vacuo and the residue was recrystalized from n-heptane to give 15 g (84%) of a white solid, mp 136°–139° C.

Anal. Calcd. for $C_{31}H_{46}O_4S$: C, 72.3; H, 8.9. Found: C, 72.2; H, 8.7.

EXAMPLE 4

S-(3,5-Di-tert-butyl-4-hydroxyphenyl) 3,5-Di-tert-butyl-4-hydroxy thiobenzoate The procedure of Example 3 was followed using 9.6 g of 2,6-di-tert-butyl-4-mercaptophenol, 10.8 g of 3,5-di-tert-butyl-4-hydroxybenzoyl chloride, and 3.6 g of pyridine. The residue was recrystallized from acetonitrile to give 8.8 g (47%) of white crystals, mp 184°–186° C.

Anal. Calcd. for $C_{29}H_{42}O_3S$; C, 74.0; H, 9.0. Found: C, 73.9; H, 8.7.

EXAMPLE 5

(a)

1-(3,5-Di-tert-butyl-4-hydroxyphenylthio)-1-hydroxymethane

To a stirred solution of 28.6 g of 2,6-di-tert-butyl-4-mercaptophenol and 9.74 g of 37% aqueous formaldehyde in 100 ml of methyl alcohol was added several drops of a 10 M potassium hydroxide solution. The reaction mixture was stirred for 13 hours and the volatiles were removed in vacuo. The residue was recrystallized from petroleum ether to give a white solid, m.p. 79°–82° C.

Analysis: Calcd. for $C_{15}H_{24}O_2S$: C, 67.1; H, 9.0; S, 11.9. Found: C, 66.8; H, 8.6; S, 11.6.

(b) 3,5-Di-tert-butyl-4-hydroxyphenylthiomethyl 3,5-Di-tert-butyl-4-hydroxybenzoate A solution of 6.71 g of the compound of example 5a), 6.26 g of 2,6-di-tert-butyl-4-hydroxybenzoic acid, 6.56 g of triphenylphosphine and 4.36 g of diethyl azodicarboxylate in 100 ml of tetrahydrofuran was stirred at 40° C. for 24 hours. The solvent was removed in vacuo and the product isolated by chromatography. IR spectrum gives an ester carbonyl absorption at 1720 $cm^{-1}$ and a phenolic OH absorption at 3610 $cm^{-1}$.

EXAMPLE 6

Stabilization of polypropylene (Light stability)

Unstabilized polypropylene powder (Hercules Profax 6501) was thoroughly blended with 0.2%, by weight, of additive. The blended materials were then milled on a two roll mill at 182° C. for five minutes, after which time the stabilized polypropylene was sheeted from the mill and allowed to cool. The milled polypropylene was then cut into pieces and compression molded on a hydraulic press at 220° C. (175 psi) into 5 mil (0.13 mm) films. The sample was exposed in a fluorescent sunlight/black light chamber until failure. Failure was determined when the film showed the first signs of decomposition (e.g. cracking or brown edges).

| Additive | Hours to failure |
| --- | --- |
| None | 200–300 |
| Compound of Example 1 | 550 |
| Compound of Example 2 | 590 |
| Compound of Example 3 | 520 |
| Compound of Example 4 | 550 |

EXAMPLE 7

Stabilization of polypropylene (oxidation stability)

The oxidation stability of milled polypropylene containing 0.2% of additive as well as that of the synergized formulation containing 0.1% of additive in the presence of 0.3% distearylthiodipropionate (DSTDP) on plaques of 25 mil (0.64 mm) thickness as determined by exposing said plaques to air in a forced draft oven at 150° C. The plaques were considered to have failed on showing the first signs of decomposition (e.g., cracking or brown edges).

| Additive | Hours to failure | |
|---|---|---|
| | 0.2% | 0.1% + 0.3% DSTDP |
| Base Resin | <20 | <20 |
| Compound of Example 1 | 300 | 980 |
| Compound of Example 2 | 250 | 1200 |
| Compound of Example 3 | 70 | 110 |
| Compound of Example 4 | 60 | 90 |

EXAMPLE 8

This example illustrates the stabilizing effectiveness of the instant stabilizer in impact polystryene.

In a laboratory procedure utilized herein, a solution of eight (8) weight percent polybutadiene rubber (Firestone - DIENE 55) dissolved in styrene monomer is prepared on a roller mill. The indicated amount of stabilizer is also introduced at this point. 500 ppm of zinc stearate are added to aid in removing the sample from the bottle after the polymerization. The bottle is screwed into the polymerization apparatus which is equipped with a double helical ribbon stirrer. Since most commercial IPS bulk polymerizations are thermally initiated processes, no initiator is used in the laboratory process. A nitrogen atmosphere is established and the reactor is then heated to 121° C. within ½ hour. Heating continues at 121° C. with efficient stirring until there is a 30 to 35% monomer conversion (2.5 hours). The stirring rate is controlled to yield to a two to four μm rubber particle size. The bottles are removed from the polymerization apparatus, blanketed ith nitrogen, capped, and then placed in a fluidized bed sand bath to complete the polymerization. The bottles are heated in the bath in the following fashion: one hour at 100° C. to equilibrate the temperature, one hour to reach 140° C. and then an additional eight hours with the temperature increasing at the rate of 10° C. per hour to a maximum of 220° C. After the resin has cooled, the bottle is broken and the glass removed. The average weight of the polymer block is slightly over 600 grams. The block is then placed into a vacuum oven at 200° C. and a vacuum of 1 mm applied as the polymer is heated for 45 minutes in order to remove all volatiles. The block is removed from the oven, immediately placed in a heated (205° C.) hydraulic press and then pressed into a thick slab between two sheets of aluminum foil (three minutes heating, five minutes in a cold press). The slab is split with a hand saw and the pieces are granulated.

All batches are extruded at 205° C. and then pelletized. The pellets are compression molded at 205° C. into 125 mil (3.175 mm) tensile bars. The bars are then aged at 150° C. on glass plates placed on rotating shelves in a forced air oven. Other tensile bars are aged at 80° C. suspended from rotating shelves in a forced air oven. The specimen yellowness index is determined on the bars at various intervals according to ASTM D-1925-63T. Correspondingly, the bars are periodically measured for percent elongation in the Instron Tensile Testing Apparatus (Instron Engineering Corporation, Massachusetts) at a pull rate of 5 mm/minute according to ASTM D-638.

| | | Oven Aged Samples @ 80° C. | | | |
|---|---|---|---|---|---|
| Additive | Additive Conc. | Hours at 80° C. | | | |
| Compound of | (% by weight) | 0 | 300 | 600 | 900 |
| | | % Elongation | | | |
| None | — | 33 | 9 | 3 | 3 |
| Example 2 | 0.1 | 23 | 19 | — | — |
| Example 4 | 0.1 | 52 | 28 | 11 | 7 |
| | | Yellowness Index | | | |
| None | — | 7 | 14 | 45 | 59 |
| Example 2 | 0.1 | 0 | 20 | 29 | 52 |
| Example 4 | 0.1 | −1 | 12 | 15 | 32 |
| | | Oven Aged Samples @ 150° C. | | | |
| Additive | Additive Conc. | Hours at 80° C. | | | |
| Compound of | (% by weight) | 0 | ½ | 1 | 1½ | 2 |
| | | % Elongation | | | |
| None | — | 33 | 7 | 7 | 3 | 3 |
| Example 2 | 0.1 | 23 | 16 | 13 | 7 | 7 |
| Example 4 | 0.1 | 52 | 32 | 8 | 7 | 7 |
| | | Yellowness Index | | | |
| None | — | 7 | 18 | 30 | 38 | 43 |
| Example 2 | 0.1 | 0 | 2 | 5 | 8 | 14 |
| Example 4 | 0.1 | −1 | 4 | 5 | 8 | 14 |

Examples 6, 7 and 8 thus indicate the significantly better performance of the instant compounds as compared to the base resin.

Summarizing, it is seen that this invention provides a group of compounds which have excellent stabilizing activity in a variety of organic materials. Variations may be made in proportions, procedures and materials without departing from the scope of the invention as defined by the following claims.

What is claimed is:

1. A composition of matter comprising an organic material subject to oxidative thermal and actinic degradation stabilized with an effective stabilizing amount of a compound of formula I

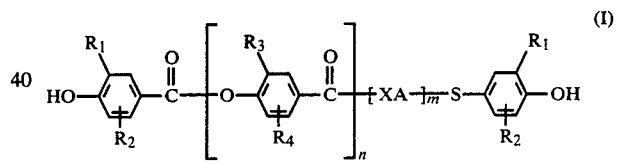

wherein
$R_1$, $R_2$, $R_3$ and $R_4$ are independently hydrogen, alkyl of 1 to 12 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms.

X is —NH— or —S—;
A is alkylene of 1 to 10 carbon atoms, phenylene or cycloalkylene of 5 to 6 carbon atoms,
m is 1, and
n is 0 or 1.

2. A composition according to claim 1 where in the compound of formula I, $R_3$ and $R_4$ are the same as $R_1$ and $R_2$ respectively and all of them are in the ortho position to the hydroxyl group.

3. A composition according to claim 2 where in the compound of formula I, $R_1$, $R_2$, $R_3$ and $R_4$ are each tert-butyl.

4. A composition according to claim 1 where in the compound of formula I, A is ethylene.

5. A composition according to claim 1 where in the compound of formula I, X is —NH—.

6. A composition according to claim 1 where in the compound of formula I, X is —S—.

7. The composition of claim 1, wherein the organic material is a synthetic polymer.

8. The composition of claim 7, wherein said polymer is selected from the group consisting of polyolefins, impact polystyrene, acrylonitrile-butadiene-styrene resin, butadiene rubber, ethylene-propylene copolymer, ethylene-propylene-diene copolymer, styrene-butadiene copolymer and nitrile rubber.

9. A method for stabilizing an organic material against oxidative, thermal and actinic degradation which comprises incorporating into said organic material an effective stabilizing amount of a compound of formula I

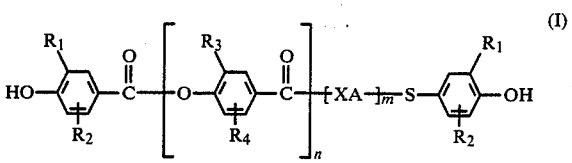

wherein
$R_1$, $R_2$, $R_3$ and $R_4$ are independently hydrogen, alkyl of 1 to 12 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms,
X is —NH— or —S—;
A is alkylene of 1 to 10 carbon atoms, phenylene or cycloalkylene of 5 to 6 carbon atoms,
m is 1, and
n is 0 or 1.

* * * * *